US00PP31157P2

(12) United States Plant Patent
Kerley et al.

(10) Patent No.: US PP31,157 P2
(45) Date of Patent: Dec. 3, 2019

(54) ***CALENDULA* PLANT NAMED 'KERCALTAN'**

(50) Latin Name: ***Calendula* x *hybrida***
Varietal Denomination: KERCALTAN

(71) Applicants: Timothy Kerley, Cambridge (GB); Sarah Kerley, Cambridge (GB); David Kerley, Cambridge (GB); Priscilla Kerley, Cambridge (GB)

(72) Inventors: Timothy Kerley, Cambridge (GB); Sarah Kerley, Cambridge (GB); David Kerley, Cambridge (GB); Priscilla Kerley, Cambridge (GB)

( * ) Notice: Subject to any disclaimer, the term of this patent is extended or adjusted under 35 U.S.C. 154(b) by 0 days.

(21) Appl. No.: 16/350,288

(22) Filed: Oct. 25, 2018

(51) Int. Cl.
*A01H 5/02* (2018.01)
*A01H 6/14* (2018.01)

(52) U.S. Cl.
USPC ..... Plt./263.1
CPC ..... *A01H 6/14* (2018.05)

(58) Field of Classification Search
USPC ..... Plt./263.1
CPC ..... A01H 5/02
See application file for complete search history.

(56) References Cited

PUBLICATIONS https://www.mandycanudigit.com/2018/05/15/rhs-chelsea-plant-of-the-year-2018/; May 15, 2018; 13 pages.*

* cited by examiner

*Primary Examiner* — Kent L Bell
(74) *Attorney, Agent, or Firm* — Cassandra Bright

(57) ABSTRACT

A *Calendula* plant named 'KERCALTAN' is disclosed, characterized by bright orange double flowers composed of only ray florets. Plants have an attractive spreading habit and flower prolifically. The flowering period is exceptionally long, from around early Spring until mid to late Fall. Plants are useful for outdoor ornamental purposes, normally produced as an outdoor garden or container plant.

3 Drawing Sheets

Genus and species: *Calendula* x *hybrida*.
Variety denomination: 'KERCALTAN'.

BACKGROUND OF THE INVENTION

'KERCALTAN' is a product of a breeding and selection program for ornamental *Calendula* varieties to be vegetatively propagated. The new plant of the present invention comprises a new and distinct cultivar of *Calendula* plant.

'KERCALTAN' is a seedling resulting from the crossing of the unpatented proprietary *Calendula hybrida* referred to as '13-36-8' with the pollen parent, an unpatented proprietary *Calendula hybrida* referred to as '13/41/6', conducted in August 2011. The selection of the new variety was made in July 2012, by the inventor at a research greenhouse located in Cambridge, UK.

'KERCALTAN' was first asexually reproduced by softwood stem cuttings at a research greenhouse in Cambridge, UK, August 2012 and has been asexually reproduced over an approximately two-year period. The new cultivar has been found to retain its distinctive characteristics through successive asexual propagations.

SUMMARY OF THE INVENTION

The following are the most outstanding and distinguishing characteristics of the new cultivar when grown under normal horticultural practices in Cambridge, UK:

1. Bright orange double flowers.
2. Quick to flower.
3. Strong tolerance to *Golovinomyces cichoracearum* powdery mildew.

COMPARISON WITH PARENT VARIETIES

Plants of the new cultivar 'KERCALTAN' are similar to plants of the seed parent in most horticultural characteristics. However, plants of the new cultivar differ in the following:

1. New variety has double flowers, while seed parent has single flowers.
2. New variety is quicker to flower than the seed parent.
3. New variety has a stronger tolerance to mildew than seed parent.
4. New variety sets less seed than seed parent.
5. Flowers of new variety has a deeper orange color than seed parent.

Plants of the new cultivar 'KERCALTAN' are similar to plants of the pollen parent in most horticultural characteristics. However, plants of the new cultivar differ in the following:

1. New variety has double flowers, while pollen parent has single flowers.
2. New variety is quicker to flower than the pollen parent.
3. New variety has better branching than pollen parent.
5. Flowers of new variety has a deeper orange color than pollen parent.

COMPARISON WITH COMMERCIAL CULTIVAR

'KERCALTAN' can be compared to the commercial variety 'KERCALDIVA', unpatented. However, 'KERCALTAN' differs in the following:

1. 'Kercaltan' plant habit is spreading. 'Kercaldiva' has a more upright habit.

2. Flowers of the new variety are a lighter orange than comparator.
3. The new variety has better branching than comparator.
4. The new variety sets less seed than comparator.
5. 'Kercaltan' has no disc florets, 'Kercaldiva' does sometimes have disc florets.

'KERCALTAN' can be compared to the commercial variety 'Cheers Orange', unpatented. However, 'KERCALTAN' differs in the following:

1. 'Kercaltan' plant habit is spreading to semi-trailing. 'Cheers Orange' has an upright habit.
2. 'Kercaltan' has better branching than comparator.
3. 'Kercaltan' sets less seed than comparator.
4. 'Kercaltan' has no disc florets, 'Cheers Orange' often has disc florets.
5. 'Kercaltan' color is stable, 'Cheers Orange' flower color fades towards yellow in high temperature/light.
6. 'Kercaltan' is highly tolerant of powdery mildew. 'Cheers Orange' is susceptible to powdery mildew.

DESCRIPTION OF THE PHOTOGRAPHS

The present invention of a new and distinct variety of *Calendula* is shown in the accompanying photographs, the colors being as nearly true as possible with color photographs of this type.

DESCRIPTION OF THE INVENTION

Figure 1:
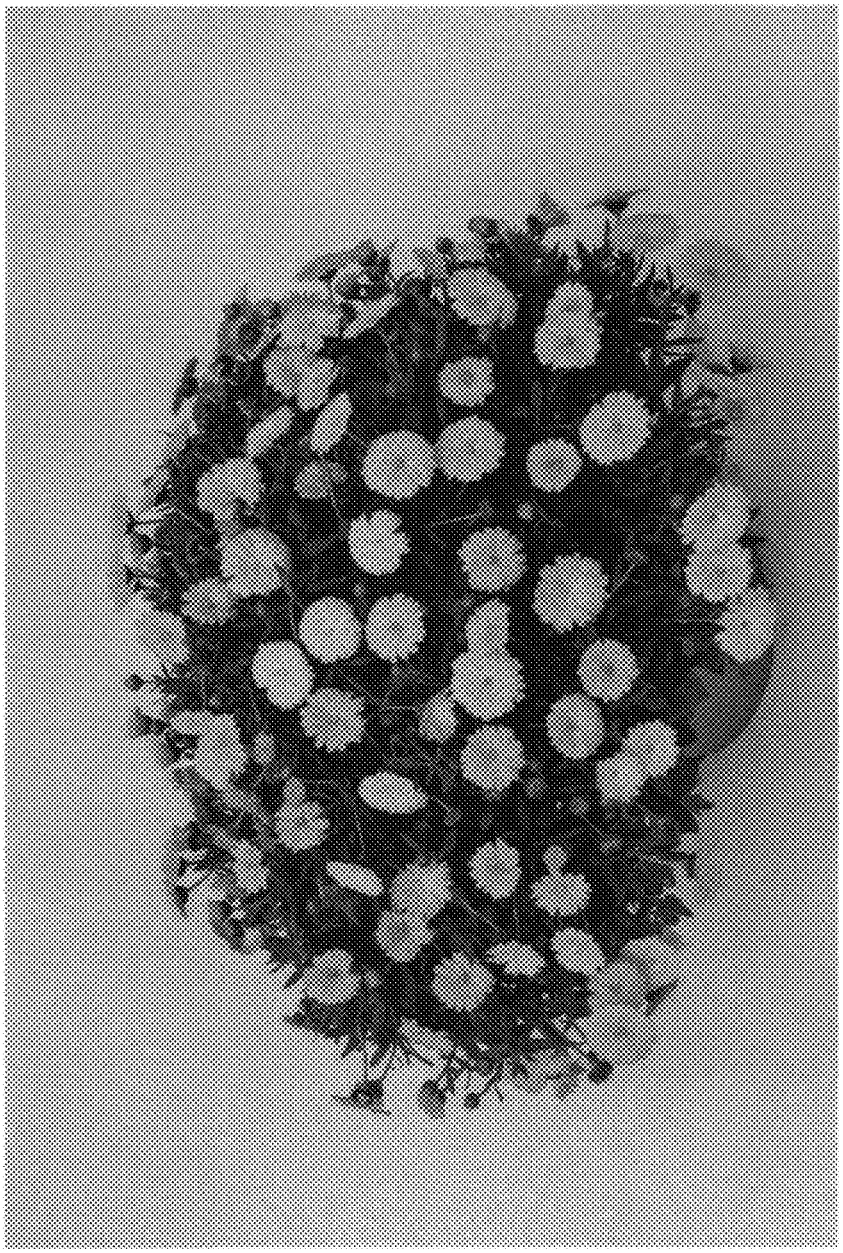
FIG. 1 illustrates a close up of the inflorescence.
Figure 2:
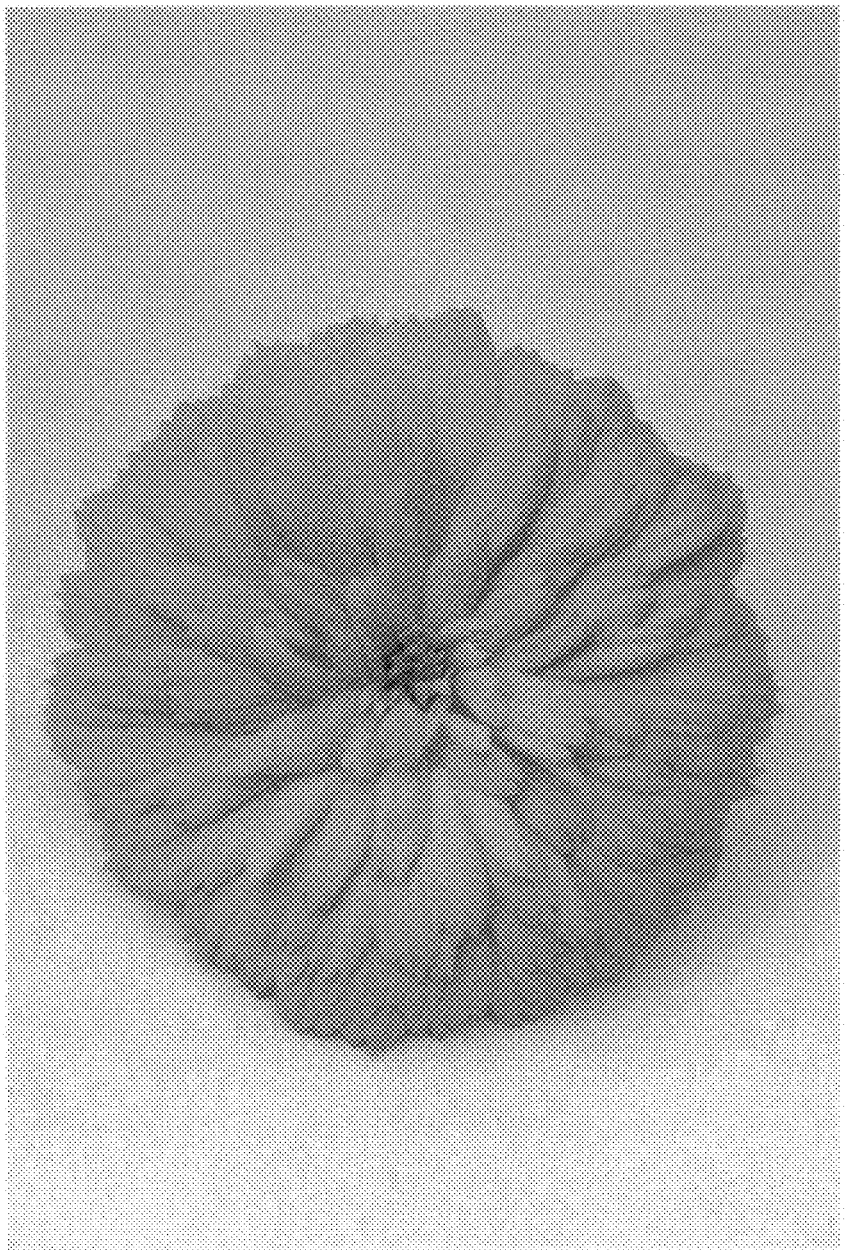
FIG. 2 illustrates a mature plant of approximately 2 years, photographed during September in Cambridge, UK.
Figure 3:
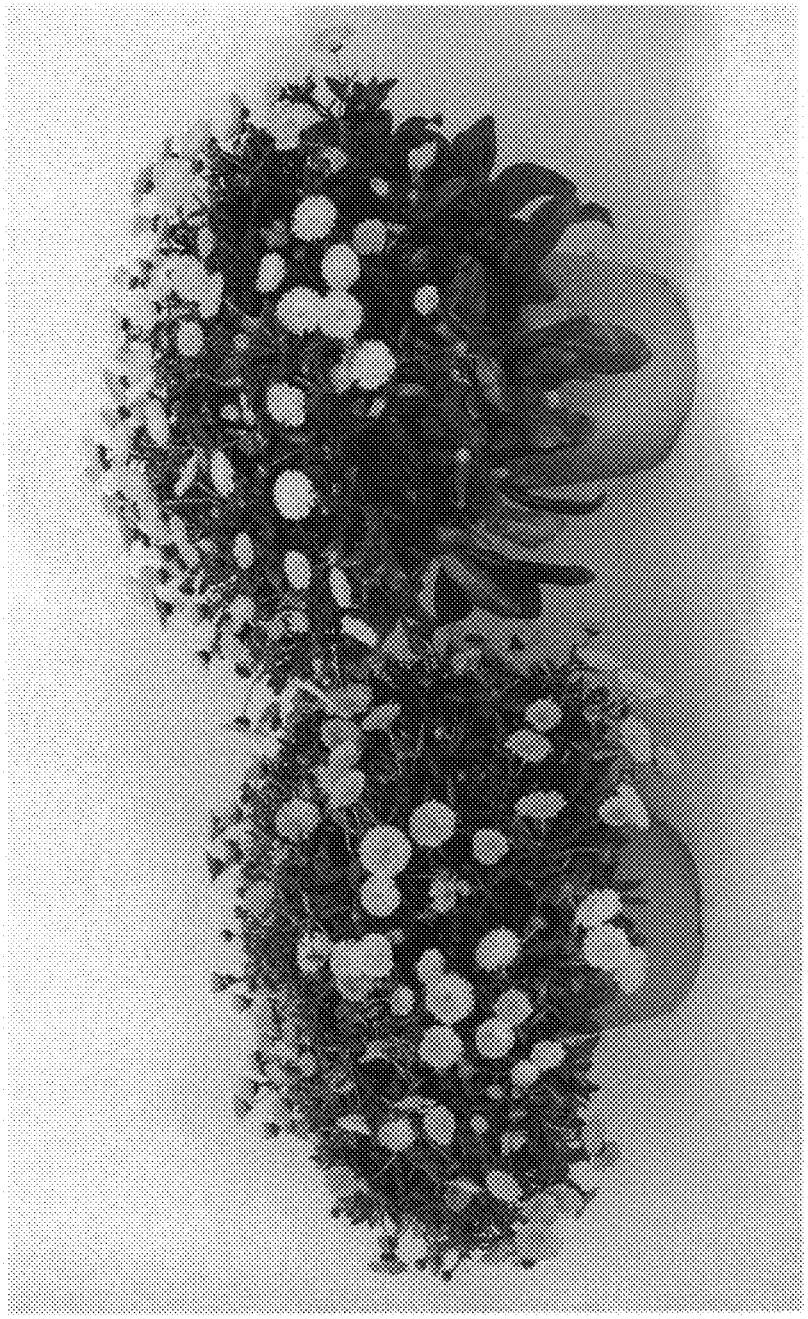
FIG. 3 illustrates a plant of 'Kercaltan' on the left side of the figure, 'Cheers Orange' is the taller plant on the right side of the figure.

This new variety of *Calendula* is of the botanical classification *Calendula hybrida*. The observations and measurements were gathered from 6 month old plants grown outdoors in Cambridge, UK under natural light, natural day length and temperatures.

The following is a description of the plant and characteristics that distinguish 'KERCALTAN' as a new and distinct variety. The color designations are taken from the plant itself. Accordingly, any discrepancies between the color designations and the colors depicted in the photographs are due to photographic tolerances. The color chart used in this description is The Royal Horticultural Society color chart, edition 1995.

DETAILED BOTANICAL DESCRIPTION

Classification:
- *Botanical.*—*Calendula hybrida.*
- *Denomination.*—'KERCALTAN'.

PROPAGATION

Typical method: Softwood stem cuttings.
Root description: Fine and fibrous brown to tan roots, not accurately measured with R.H.S. chart.

PLANT

Shape: Compact, spreading.
Growth habit: Herbaceous perennial.
Growth rate: Moderate.
Height: 19 cm.
Width: 26 cm.

Branches/stems:
- *Color.*—Near RHS Yellow-Green 146D.
- *Strength.*—Strong.
- *Length of lateral branch.*—21 cm.
- *Diameter of lateral branch.*—0.6 cm.
- *Aspect.*—Approximately 45 degrees.
- *Average number of lateral branches.*—3 to 4 main stems, with 4 to 5 lateral branches.
- *Internode length.*—Average 2.2 cm.

FOLIAGE

Leaf:
- *Arrangement.*—Alternate.
- *Average length.*—6 cm.
- *Average width.*—2.5 cm.
- *Shape of blade.*—Oblanceolate.
- *Apex.*—Acute on young leaves, more obtuse on mature leaves.
- *Base.*—Truncate.
- *Attachment.*—Decurrent.
- *Margin.*—Entire.
- *Texture of top surface.*—Slightly pubescent.
- *Texture of bottom surface.*—Smooth.
- *Color.*—Young foliage upper side: Near RHS Green 137A. Young foliage under side: Near RHS Green 137B. Mature foliage upper side: Near RHS Green 137B. Mature foliage under side: Near RHS Yellow-Green 147B.
- *Venation.*—Type: Pinnate. Venation color upper side: RHS Yellow-Green 146B. Venation color under side: RHS Yellow-Green 146C/D (each color individually present).

FLOWER

Bloom period: March until November in Cambridge, UK.
Bud:
- *Bud shape.*—Ovoid.
- *Bud length.*—1.2 cm.
- *Bud diameter.*—1.1 cm.
- *Bud color.*—RHS Yellow-Green 147B.

Inflorescence:
- *Form.*—Terminal capitulum of ray florets only.
- *Quantity per plant.*—25 per plant, 3 to 6 per lateral stem.
- *Diameter.*—5.5 cm.
- *Depth.*—2 cm.

Ray florets:
- *Number of ray florets.*—Average 125.
- *Arrangement.*—5 to 6 whorls.
- *Length.*—Approximately 2.3 cm.
- *Width.*—Approximately 0.4 cm.
- *Apex shape.*—Obtuse.
- *Base.*—Narrow cuneate.
- *Margin.*—Entire, apex serrate.
- *Color.*—Upper surface at first opening: RHS Orange N25B. Under surface at first opening: RHS Orange N25C. Upper surface at maturity: Brighter than RHS Orange 23A, base Yellow-Orange 17A. Under surface at maturity: RHS Orange 23A, base Yellow-Orange 14B.

Disc florets: None observed.
Fragrance: None

Phyllaries/involucral bracts:
*Number*.—Average 28, in a single whorl.
*Length*.—Approximately 0.8 cm.
*Width*.—Approximately 0.2 cm.
*Texture*.—Upper: Pubescent. Lower: Glabrous.
*Shape*.—Oblanceolate.
*Apex*.—Acute.
*Margin*.—Entire.
*Color*.—Upper surface: RHS Green 137A. Lower surface: RHS Yellow-Green 147B.
Peduncle:
*Peduncle length*.—5.3 cm.
*Peduncle diameter*.—0.3 cm.
*Aspect*.—Mostly nearly vertical, some at approximately 45 degrees to main stem.
*Color*.—Near RHS Yellow-Green 144A.
*Peduncle texture*.—Pubescent.
Receptacle:
*Shape*.—Truncate.
*Length*.—0.5 cm.
*Diameter*.—0.9 cm.
*Color*.—RHS Yellow-Green 146C.

REPRODUCTIVE ORGANS

Ray florets:
Gynoecium:
*Pistil number*.—1.
*Pistil length*.—0.6 cm.
*Style length*.—0.2 cm.
*Style color*.—Near RHS Green-Yellow 1C.
*Stigma shape*.—Biparted.
*Stigma color*.—Near RHS Yellow-Orange 17A.
*Ovary diameter*.—1 mm.
*Ovary color*.—Near RHS Yellow 1D.
Androecium: Not present.

OTHER CHARACTERISTICS

Disease and pest resistance: Strong resistance to powdery mildew, the exact pathogen is unconfirmed, possibly *Golovinomyces cichoracearum*. Neither resistance nor susceptibility to additional normal diseases and pests of *Calendula* has been observed.
Cold tolerance: Short lived hardy perennial, tolerating low temperatures to approximately −10 degrees C.
Fruit/seed production: Not observed.

What is claimed is:
1. A new and distinct variety of *Calendula* plant named 'KERCALTAN' as described and shown herein.

* * * * *